United States Patent [19]
Anker et al.

[11] Patent Number: 5,457,045
[45] Date of Patent: Oct. 10, 1995

[54] ENZYMES WITH XYLANOLYTIC ACTIVITY

[75] Inventors: Lisbeth Anker, Copenhagen; Henrik Bisgård-Frantzen, Lyngby; Torben Halkier, Frederiksberg, all of Denmark

[73] Assignee: Novo Nordisk A/S, Bagsvaerd, Denmark

[21] Appl. No.: 978,692

[22] PCT Filed: Aug. 23, 1991

[86] PCT No.: PCT/DK91/00242

§ 371 Date: Feb. 2, 1993

§ 102(e) Date: Feb. 2, 1993

[87] PCT Pub. No.: WO92/03540

PCT Pub. Date: Mar. 5, 1992

[30] Foreign Application Priority Data

Feb. 22, 1991 [DK] Denmark ................... 0309/91
Aug. 24, 1990 [WO] WIPO ............... PCT/DK91/00242

[51] Int. Cl.$^6$ ..................................... C12N 9/26
[52] U.S. Cl. .................. 435/201; 435/200; 435/320.1; 435/172.3
[58] Field of Search ................. 435/201, 320.1, 435/252.3, 252.31, 172.3; 536/23.1, 23.2; 935/9, 14, 29, 60; 930/240

[56] References Cited

FOREIGN PATENT DOCUMENTS 61-39036  9/1986  Japan.
WO91/02839  3/1991  WIPO.

OTHER PUBLICATIONS

Okada et al., Chemical Abstracts, vol. 109, No. 25, p. 340, Abstract No. 225224v, 1988.
Moriyama et al., Chemical Abstracts, vol. 107, No. 25, p. 199, Abstract No. 230230g.
Noe et al., Chemical Abstracts vol. 105, No. 10, p. 115, Abstract No. 80961p.
Fukusaki et al., FEBS, vol. 171, No. 2, pp. 197–201, Jun. 1984.
Paice et al., Biotechnology and Bioengineering, vol. 32, pp. 235–239, 1988.
D. J. Senior et al., Biotechnology and Bioengineering, vol. 37, pp. 274–270, 1991.
W. Panbangred et al., Agric. Biol. Chem., vol. 47, No. 5, pp. 957–963, 1983.
Akiba et al. 1988 Meth. Enzymol. 160, 655–659.
Sjoblom et al. "Reduced Discharge of TOCl with a Hot (EO) Stage") 1988 Int'l–Pulp Bleaching Conf. Jun. 5–9, 1988 Orlando, Fla.

Primary Examiner—Christopher S. F. Low
Attorney, Agent, or Firm—Steve T. Zelson; Elias J. Lambiris

[57] ABSTRACT

This invention relates to novel enzymes possessing xylanolytic activity. More specifically, the invention relates to novel xylanases obtainable from strains of *Bacillus pumilus*, a process for their preparation, and the use of these xylanases for treatment of lignocellulosic pulp.

4 Claims, 4 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 201 amino acids
        ( B ) TYPE: amino acid
        ( C ) STRANDEDNESS: single
        ( D ) TOPOLOGY: linear     ( i i ) MOLECULE TYPE: protein     ( v i ) ORIGINAL SOURCE:
        ( A ) ORGANISM: Bacillus pumilus
        ( B ) STRAIN: IPO     ( x ) PUBLICATION INFORMATION:
        ( A ) AUTHORS: Fukusaki, E.
                Panbangred, W.
                Shinmyo, A.
                Okada, H.
        ( B ) TITLE: The complete nucleotide sequence of the
                xylanase gene (xynA) of Bacillus pumilus
        ( C ) JOURNAL: FEBS Lett.

(D) VOLUME: 171
(E) ISSUE: 2
(F) PAGES: 197-201
(G) DATE: 1984

(xi) SEQUENCE DESCRIPTION: SEQ ID NO:1:

| | | | | | | | | | | | | | | |
|---|---|---|---|---|---|---|---|---|---|---|---|---|---|---|
| Arg | Thr | Ile | Thr | Asn | Asn | Glu | Met | Gly | Asn | His | Ser | Gly | Tyr | Asp | Tyr |
| 1 | | | | 5 | | | | | 10 | | | | | 15 | |
| Glu | Leu | Trp | Lys | Asp | Tyr | Gly | Asn | Thr | Ser | Met | Thr | Leu | Asn | Asn | Gly |
| | | | 20 | | | | | 25 | | | | | 30 | | |
| Gly | Ala | Phe | Ser | Ala | Gly | Trp | Asn | Asn | Ile | Gly | Asn | Ala | Leu | Phe | Arg |
| | | 35 | | | | | 40 | | | | | 45 | | | |
| Lys | Gly | Lys | Lys | Phe | Asp | Ser | Thr | Arg | Thr | His | His | Gln | Leu | Gly | Asn |
| | 50 | | | | | 55 | | | | | 60 | | | | |
| Ile | Ser | Ile | Asn | Tyr | Asn | Ala | Ser | Phe | Asn | Pro | Ser | Gly | Asn | Ser | Tyr |
| 65 | | | | | 70 | | | | | 75 | | | | | 80 |
| Leu | Cys | Val | Tyr | Gly | Trp | Thr | Gln | Ser | Pro | Leu | Ala | Glu | Tyr | Tyr | Ile |
| | | | | 85 | | | | | 90 | | | | | 95 | |
| Val | Asp | Ser | Trp | Gly | Thr | Tyr | Arg | Pro | Thr | Gly | Ala | Tyr | Lys | Gly | Ser |
| | | | 100 | | | | | 105 | | | | | 110 | | |
| Phe | Tyr | Ala | Asp | Gly | Gly | Thr | Tyr | Asp | Ile | Tyr | Glu | Thr | Thr | Arg | Val |
| | | 115 | | | | | 120 | | | | | 125 | | | |
| Asn | Gln | Pro | Ser | Ile | Ile | Gly | Ile | Ala | Thr | Phe | Lys | Gln | Tyr | Trp | Ser |
| | 130 | | | | | 135 | | | | | 140 | | | | |
| Val | Arg | Gln | Thr | Lys | Arg | Thr | Ser | Gly | Thr | Val | Ser | Val | Ser | Ala | His |
| 145 | | | | | 150 | | | | | 155 | | | | | 160 |
| Phe | Arg | Lys | Trp | Glu | Ser | Leu | Gly | Met | Pro | Met | Gly | Lys | Met | Tyr | Glu |
| | | | | 165 | | | | | 170 | | | | | 175 | |
| Thr | Ala | Phe | Thr | Val | Glu | Gly | Tyr | Gln | Ser | Ser | Gly | Ser | Ala | Asn | Val |
| | | | 180 | | | | | 185 | | | | | 190 | | |
| Met | Thr | Asn | Gln | Leu | Phe | Ile | Gly | Asn | | | | | | | |
| | | 195 | | | | | 200 | | | | | | | | |

(2) INFORMATION FOR SEQ ID NO:2:

(i) SEQUENCE CHARACTERISTICS:
(A) LENGTH: 28 amino acids
(B) TYPE: amino acid
(D) TOPOLOGY: linear (v) FRAGMENT TYPE: N-terminal (vi) ORIGINAL SOURCE:
(A) ORGANISM: Bacillus pumilus
(B) STRAIN: DSM 6124

(xi) SEQUENCE DESCRIPTION: SEQ ID NO:2:

| | | | | | | | | | | | | | | |
|---|---|---|---|---|---|---|---|---|---|---|---|---|---|---|
| Glu | Thr | Ile | Tyr | Asp | Asn | Arg | Ile | Gly | Arg | His | Thr | Gly | Tyr | Asp | Phe |
| 1 | | | | 5 | | | | | 10 | | | | | 15 | |
| Glu | Leu | Trp | Lys | Asp | Tyr | Gly | Asn | Thr | Ser | Met | Ile | | | | |
| | | | 20 | | | | | 25 | | | | | | | |

(2) INFORMATION FOR SEQ ID NO:3:

(i) SEQUENCE CHARACTERISTICS:
(A) LENGTH: 31 amino acids
(B) TYPE: amino acid
(D) TOPOLOGY: linear (v) FRAGMENT TYPE: internal (vi) ORIGINAL SOURCE:

(A) ORGANISM: Bacillus pumilus
(B) STRAIN: DSM 6124

(x i) SEQUENCE DESCRIPTION: SEQ ID NO:3:

```
Ser Ala Ser Trp Asn Asn Ile Gly Asn Ala Leu Phe Arg Lys Gly Lys
1               5                   10                  15

Lys Phe Asp Ser Thr Lys Thr His His Gln Leu Gly Asn Ile Asp
            20              25                  30
```

(2) INFORMATION FOR SEQ ID NO:4:

(i) SEQUENCE CHARACTERISTICS:
       (A) LENGTH: 104 amino acids
       (B) TYPE: amino acid
       (D) TOPOLOGY: linear (v) FRAGMENT TYPE: C-terminal (v i) ORIGINAL SOURCE:
       (A) ORGANISM: Bacillus pumilus
       (B) STRAIN: DSM 6124

(x i) SEQUENCE DESCRIPTION: SEQ ID NO:4:

```
Ile Val Glu Ser Trp Gly Thr Tyr Arg Pro Thr Gly Thr Tyr Lys Trp
1               5                   10                  15

Ser Phe Tyr Ala Asp Gly Gly Thr Tyr Asp Ile Tyr Glu Thr Leu Arg
            20                  25                  30

Val Asn Gln Pro Ser Ile Ile Gly Asp Ala Thr Phe Lys Gln Tyr Val
        35                  40                  45

Ser Val Arg Gln Thr Lys Arg Thr Ser Gly Thr Val Ser Val Ser Glu
    50                  55                  60

His Phe Lys Lys Trp Glu Gly Leu Tyr Met Pro Met Gly Lys Met Tyr
65                  70                  75                  80

Glu Thr Ala Leu Thr Val Glu Gly Tyr Arg Ser Thr Gly Ser Ala Asn
                85                  90                  95

Val Met Thr Asn Gln Leu Met Ile
            100
```

(2) INFORMATION FOR SEQ ID NO:5:

(i) SEQUENCE CHARACTERISTICS:
       (A) LENGTH: 16 amino acids
       (B) TYPE: amino acid
       (C) STRANDEDNESS: single
       (D) TOPOLOGY: linear (i i) MOLECULE TYPE: peptide (v) FRAGMENT TYPE: internal (x i) SEQUENCE DESCRIPTION: SEQ ID NO:5:

```
Ile Val Glu Ser Trp Gly Thr Tyr Arg Pro Thr Gly Thr Tyr Lys Gly
1               5                   10                  15
```

(2) INFORMATION FOR SEQ ID NO:6:

(i) SEQUENCE CHARACTERISTICS:
       (A) LENGTH: 23 amino acids
       (B) TYPE: amino acid
       (C) STRANDEDNESS: single
       (D) TOPOLOGY: linear (i i) MOLECULE TYPE: peptide (v) FRAGMENT TYPE: internal ( x i ) SEQUENCE DESCRIPTION: SEQ ID NO:6:

Val Asn Gln Pro Ser Ile Ile Gly Asp Ala Thr Phe Lys Gln Tyr Val
1               5                       10                      15

Ser Val Arg Gln Thr Lys Arg
              20

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:7:

His Phe Lys Lys Xaa Glu Gly Leu
1               5

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:8:

Thr Val Ala Gly Tyr
1               5

ENZYMES WITH XYLANOLYTIC ACTIVITY

CROSS-REFERENCE TO RELATED APPLICATIONS

This application is a continuation of PCT/DK91/00242 filed Aug. 23, 1991, which is incorporated herein by reference.

FIELD OF THE INVENTION

This invention relates to novel enzymes possessing xylanolytic activity. More specifically, the invention relates to novel xylanases obtainable from strains of Bacillus pumilus, a process for their preparation, and the use of these xylanases for treatment of lignocellulosic pulp.

BACKGROUND ART

Members of Bacillus pumilus are known and described in the literature, and it is known that they are able to produce xylanases.

A specific isolate from soil in Thailand, B. pumilus IPO, has been thoroughly described by Panbangred et al. (1983); J. Agric. Biol. Chem.; 47(5), 957–963; and Fukusaki et al. (1984); FEBS Lett.; 171(2), 197–201. In JP Patent Specification No. 86039036, this B. pumilus IPO xylanase is provided by way of recombinant DNA technology. The specification mentions the use of this enzyme in the decomposition of xylan contained in animal feed or in clarification of muddy wines or fruit juices. There is given no indication of its usefulness in the treatment of lignocellulosic pulp.

SUMMARY OF THE INVENTION

Now a novel xylanase obtainable from a strain of B. pumilus has been elucidated. The xylanase of this invention possesses excellent properties for treatment of lignocellulosic pulp.

Accordingly, in its first aspect, the present invention provides xylanases comprising specified partial amino acid sequences, and having immunochemical properties identical or partially identical to those of a xylanase derived from the strain DSM, No. 6124.

In another aspect, the invention provides xylanases comprising specified partial amino acid sequences, and being obtainable from strains of Bacillus pumilus, or a mutant or a variant thereof.

The invention also provides a method of producing the xylanases, comprising cultivation of a strain of B. pumilus, or a mutant or a variant thereof, in a nutrient medium containing assimilable carbon and nitrogen together with other essential nutrient, followed by recovery of the desired enzyme.

In a further aspect, the invention provides a method of producing the xylanases, comprising isolating a DNA fragment encoding the xylanase; combining the DNA fragment with an appropriate expression signal in an appropriate plasmid vector; introducing the plasmid vector into an appropriate host either as an autonomously replicating plasmid or integrated into the chromosome; cultivating the host organism under conditions leading to expression of the xylanase; and recovering the xylanase from the culture medium.

Moreover, the invention relates to the use of the xylanases in the treatment of lignocellulosic pulp. In a more specific aspect, the invention provides a process for treatment of lignocellulosic chemical pulp, wherein the lignocellulosic pulp is treated with the xylanase at a pH of above 6.5, preferably above 7.5, whereafter the thus treated cellulosic pulp is treated with chlorine at an active chlorine multiple of 0.20 or less in the first chlorination stage.

BRIEF DESCRIPTION OF DRAWINGS

The present invention is further illustrated by reference to the accompanying drawings, in which.

DETAILED DISCLOSURE OF THE INVENTION

The present invention provides novel xylanases. These novel xylanases are especially useful for treatment of lignocellulosic pulp.

The enzymes

The novel xylanases of the invention are obtainable from Bacillus pumilus, DSM No. 6124 (deposited on Jul. 23, 1990 at Deutsche Sammlung von Mikroorganismen under the conditions of the Budapest Treaty), or mutants or variants thereof.

By an enzyme variant or mutated enzyme is meant an enzyme obtainable by alteration of the DNA nucleotide sequence of the parent gene or its derivatives. The enzyme variant or mutated enzyme may be expressed and produced when the DNA nucleotide sequence encoding the enzyme is inserted into a suitable vector in a suitable host organism. The host organism is not necessarily identical to the organism from which the parent gene originated.

Figure 1:
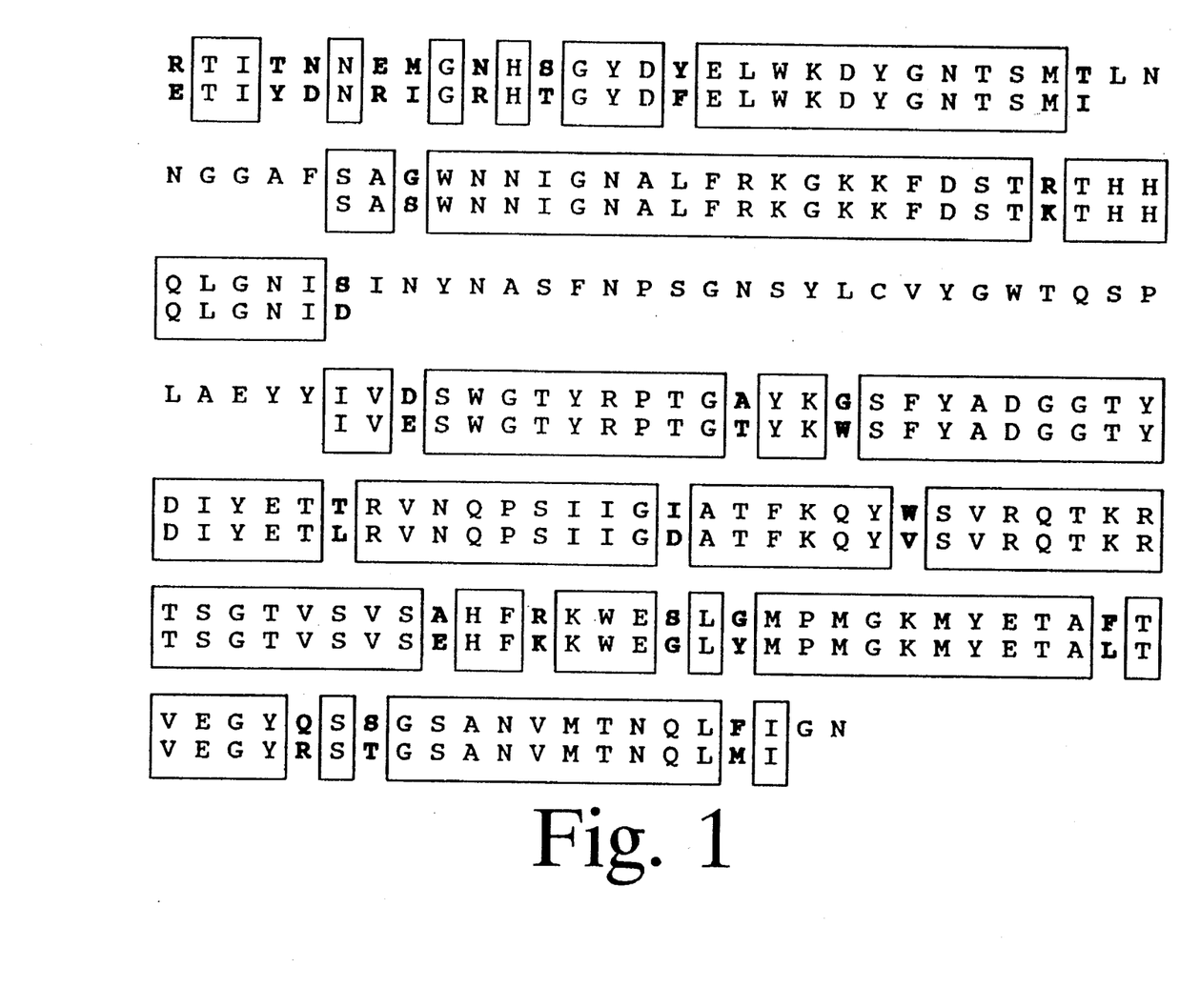
FIG. 1 shows a comparison of the amino acid sequence of the B. pumilus IPO xylanase according to Fukusaki et al. (1984), op. cit. (the upper sequence (SEQ I.D. No: 1) and the partial amino acid sequence of the xylanase of the invention (the lower sequence (SEQ. I.D. Nos. 2–4) the amino acids are indicated in the established one-letter code.

The xylanases of invention comprise the amino acid sequences that appear from FIG. 1 and Sequence Nos. 2–4 of the sequence list. On the figure the upper amino acid sequence represents the B. pumilus IPO xylanase described by Fukusaki et al. (1984), op. cit. (Seq. No. 1), and the lower amino acid sequences represent sequences that are found to be held within the amino acid sequence of a xylanase of this invention (Seq. Nos. 2–4).

The lower sequence was found after proteolytic degradation of the xylanase. Among 163 amino acid residues determined, 26 are found to be different from the B. pumilus IPO xylanase amino acid sequence published. On the figure the positions that differ between the two sequences are shown in bold typing whereas positions with identical amino acid residues are outlined.

The xylanase of the invention has immunochemical properties identical or partially identical to those of a xylanase derived from the strain DSM, No. 6124.

The immunochemical properties can be determined immunologically by cross-reaction identity tests. The identity tests can be performed by the well-known Ouchterlony double immunodiffusion procedure or by tandem crossed immunoelectrophoresis according to N.H. Axelsen; Handbook of Immunoprecipitation-in-Gel Techniques; Blackwell Scientific Publications (1983), chapters 5 and 14. The terms "antigenic identity" and "partial antigenic identity" are described in the same book, chapters 5, 19 and 20.

The molecular weight of a xylanase of this invention has been estimated to approximately 22 kDa, as determined by SDS-PAGE.

The xylanase possesses xylanolytic activity in a pH range of from below pH 5 to above pH 11. At pH 5 more than 90% relative activity are determined. The pH optimum for the xylanase is in the range of from pH 5 to pH 7, around pH 6.

The temperature profile for the xylanase is very broad, and the xylanase has no distinct temperature optimum. The xylanase is found to be nearly as active at 60° C., with around 95% persisting relative activity, as at 40° C. The temperature optimum is found to be lower than 70° C., where only around 5% of the xylanase activity persist.

The pI for the purified xylanase was found to be within the range of from 8.0 to 9.5, around 8.8.

The amino acid composition of the xylanase has been determined after acid hydrolysis and it is found to differ from the amino acid composition of the *B. pumilus* IPO xylanase, especially in the content of serine and glycine, as shown in Table 1.

TABLE 1

| Amino acid | *B. pumilus* xylanase amino acid composition (mol-%) | *B. pumilus* xylanase amino acid composition according to molecular weight (residues) | *B. pumilus* IPO xylanase amino acid composition calculated from the amino acid sequence (residues) |
|---|---|---|---|
| Asx | 11.5 | 22 | 24 |
| Glx | 7.5 | 14 | 14 |
| Ser | 7.9 | 15 | 20 |
| Gly | 10.0 | 19 | 23 |
| His | 2.0 | 4 | 4 |
| Arg | 4.3 | 8 | 8 |
| Thr | 9.4 | 18 | 19 |
| Ala | 5.5 | 11 | 11 |
| Pro | 2.6 | 5 | 5 |
| Tyr | 7.6 | 15 | 16 |
| Val | 4.1 | 8 | 8 |
| Met | 2.7 | 5 | 6 |
| Cys | 0.5 | 1 | 1 |
| Ile | 4.6 | 9 | 10 |
| Leu | 5.4 | 10 | 8 |
| Phe | 4.4 | 8 | 9 |
| Lys | 5.9 | 11 | 9 |
| Trp | 4.1 | 8 | 6 |
| Total | 100.0 | 191 | 201 |

The preparation

The xylanases of the invention are producible by cultivation of a xylanase producing strain of *Bacillus pumilus*, preferably *B. pumilus*, DSM No. 6124, or a mutant or a variant thereof.

Xylanase producing *B. pumilus* strains can be cultivated under aerobic conditions in a nutrient medium containing assimilable carbon and nitrogen together with other essential nutrient. The medium can be composed in accordance with principles known in the art.

During cultivation, the cells secrete xylanases extracellularly, so the recovery of xylanases preferably includes separation of cell mass from the cell broth while avoiding cell lysis, e.g. by filtration or centrifugation.

The resulting cell-culture can be used as such, optionally after concentration e.g. by evaporation or ultrafiltration. If desired, the xylanases can be separated and purified to the desired degree by conventional methods, e.g. by column chromatography.

The xylanases are also obtainable by recombinant DNA technology by methods known in the art per se, e.g. isolating a DNA fragment encoding the xylanase; combining the DNA fragment with an appropriate expression signal in an appropriate plasmid vector; introducing the plasmid vector into an appropriate host (i.e. an *Escherichia coli*, or a member of the genus *Bacillus, Aspergillus, or Streptomyces*), either as an autonomously replicating plasmid or integrated into the chromosome; cultivating the host organism under conditions leading to expression of the xylanase; and recovering the xylanase from the culture medium.

The xylanases also may be produced essentially as described in JP Patent Specification No. 86039036.

Treatment of lignocellulosic pulp

The xylanase of this invention is valuable for treatment of lignocellulosic pulp.

Xylan, a major component of plant hemicellulose, is a polymer of D-xylose linked by B-1,4-xylosidic bonds. Xylan can be degraded to xylose and xylo-oligomers by acid or enzymatic hydrolysis. Enzymatic hydrolysis of xylan produces free sugars without the by-products formed with acid (e.g. furans).

The pulp and paper industry is using xylanase compositions in the bleaching process to enhance the brightness of bleached pulps, to decrease the amount of chlorine used in the bleaching stages, and to increase the freeness of pulps in the recycled paper process [Eriksson, K.E.L. (1990); Wood Science and Technology, 24, 79–101.; Paice, M.G.; Bernier, R.; & Jurasek. L. (1988); Biotechnol. and Bioeng., 32, 235–239; Pommier, J.C.; Fuentes, J.L.; & Goma, G.(1989); Tappi Journal, 187–191].

Processes for treatment of lignocellulosic pulp are widely described in the literature, vide e.g. Paice, M.G. & Jurasek, L. (1984); Journal of Wood Chemistry and Technology, 4(2), 187–198; Noe, P. et al., (1986); Journal of Wood Chemistry and Technology, 6(2), 167–184; or EP Patent Application No. 386,888.

In relation to the use of the xylanases of this invention for treatment of lignocellulosic pulp, a particular process is described in International Patent Publication No. WO 91/02839, which publication is hereby included by reference.

The invention is further illustrated in the following examples which are not intended to be in any way limiting to the scope of the invention as claimed.

EXAMPLE 1

Production of Bacillus pumilus Xylanase

A *Bacillus pumilus* culture DSM 6124 was maintained on A3-medium, at 37° C.

A3-medium:

|  | g/l |
| --- | --- |
| Peptone, Difco ™ | 6.0 |
| Yeast Extract | 3.0 |
| Pepticase ™ | 4.0 |
| Beef Extract | 1.5 |
| Glucose | 1.0 |
| Agar, Merck ™ | 20.0 |
| $H_2O$ | 1000 ml | pH adjustment to 7.3 before autoclaving.
Autoclaving 25 min./121° C.

120 shake flasks with 150 ml XYL-8 medium each, inoculated from A3-agar slants, were cultivated for 4 days, 37° C., 250 rpm with approximately 2 cm amplitude.

XYL-8 medium:

|  | g/l |
| --- | --- |
| Bacto-peptone, Difco ™ | 10.0 |
| Yeast extract | 10.0 |
| $K_2HPO_4$ | 15.0 |
| $MgSO_4.7H_2O$ | 0.5 |
| KCl | 0.1 |
| $FeSO_4.7H_2O$ | 0.01 |
| Beech xylan, Lenzing ™ | 6.0 | pH adjustment to 7.0 before autoclaving.
Autoclaving 25 min./121° C.

The broth was centrifuged for half an hour at 4,000 rpm (SORVALL RC-3B centrifuge with a 6000 A rotor). The supernatant, 7.3 l, was filtered through a 10 μm nylon filter, and concentrated by ultrafiltration by means of a Pellicon equipment from Millipore, with a 10,000MWcut-off membrane and washed 2 times with one volume of water. This resulted in 540 ml of concentrate. The concentrate was then lyophilized, whereby 8.8 g of powder were generated.

EXAMPLE 2

Purification example

The xylanase was purified in seven steps.

Approximately 500 ml of fermentation broth were centrifuged at 5000 rpm for 30 min. The supernatant was then precipitated with 50% w/w ammonium sulfate. The precipitate was dissolved in 20 mM Tris-HCl buffer, pH 7.0, and desalted and concentrated until the conductivity was less than 1 mS/cm using a Filtron ultrafiltration module with 3 kD cut off membranes.

The concentrate was applied to a 25 ml anion exchanger (Q-sepharose F.F.) equilibrated with 20 mMTris-HCl buffer, pH 7.0.

The flow-through was applied to a 25 ml cation exchanger (S-sepharose F.F.) equilibrated with the same buffer. The column was eluted with a linear gradient consisting of 200 ml of the above buffer and 200 ml added 500 mMNaCl.

Most of the remaining proteases of the fractions with xylanase activity were removed by affinity chromatography at pH 7.0.

The flow-through was added ammonium sulfate to a concentration of 20% w/w and applied on a 10 ml Phenyl-Sepharose CL-4B. The column was eluted with a linear gradient consisting of 750 ml 20 mM Tris-HCl buffer, pH 7.0, 20% w/w ammonium sulfate, and 750 ml of the same buffer without ammonium sulfate.

The fractions with xylanase activity were concentrated using an Amicon ultrafiltration unit 8200 with DDS GR90PP membranes. When the concentration of xylanase was approximately 100 mg/ml and the conductivity was 20 mS/cm, the xylanase started to crystallize.

The yield was near 100%. The crystals were dissolved in 20 mM Tris-HCl buffer, pH 7.0, 25% w/w glycerol.

EXAMPLE 3

Method for determining xylanase activity

Xylanase was determined by assaying for reducing sugars released from Birch xylan (the XU method).

The assay is performed using 0.5% Birch xylan (ROTH GmbH Atr. 7500) prepared in 40mMBritton-Robinson buffer (heat treated 30 min. at 100° C. before use) as substrate. The assay is run for 20 min. at 40° C. using 0.100 ml Enzyme Solution I (35.1 g $Na_2HPO_4$, $2H_2O$; 40.0 g $KNaC_4H_4O_6$, $4H_2O$, suspended in 500 ml deionized $H_2O$; 42 ml concentrated $H_2SO_4$; 6.0 g $Na_2HAsO_4$, $7H_2O$; ad deionized water to a total volume of 1 litre) is added. Add 2.0 ml of deionized water and measure the absorbance on a spectrophotometer (PYE UniCAM PU8600UV/VIS, Phillips) at 250 nm. The reducing sugars are calculated from a standard curve prepared with xylose (40–400 μg/ml). One XU is equivalent to 1 nmol xylose released per second per milliliter or per gram of culture broth.

EXAMPLE 4 pH characterization

The pH characterization of the xylanase was determined using the purified xylanase preparation according to Examples 1 and 2, and the XU method described in Example 3.

The characterization was performed in the range of from pH 5 to pH 11. All assays were performed for 20 min. at 40° C. The profile is presented in FIG. 2.

Figure 2:
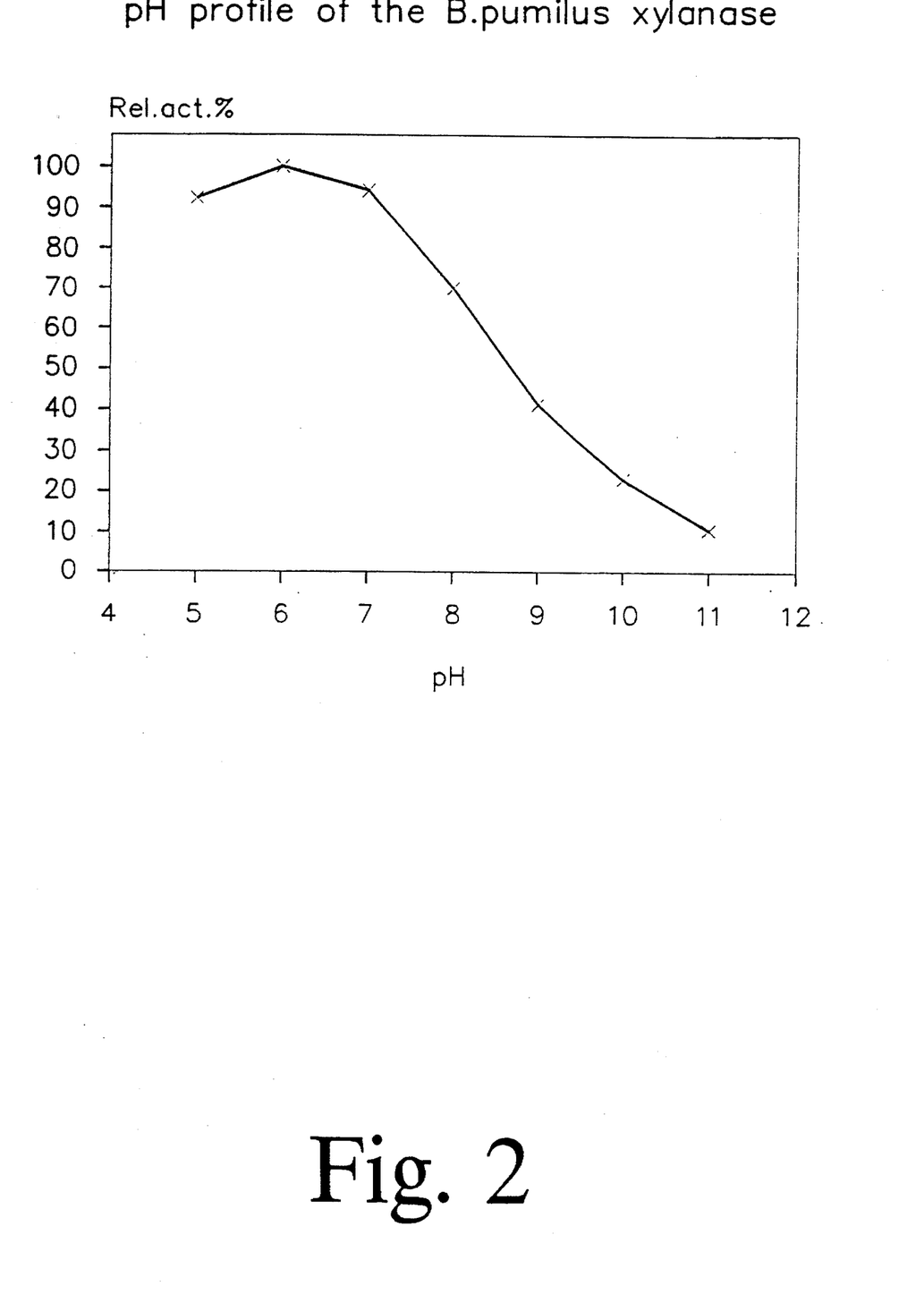
FIG. 2 shows the pH profile of a xylanase of the invention.

It appears from this characterization that the xylanase of the invention possesses xylanolytic activity from below pH 5 to above pH 11. At pH 5 a relative activity of more than 90% has been determined. At pH 9 a relative activity of more than 40% has been determined. At pH 11 a relative activity of more than 10% has been determined.

The pH optimum for the xylanase is in the range of from pH 5 to pH 7, around pH 6.

EXAMPLE 5

Temperature characterization

The temperature characterization of the xylanase was determined using the purified xylanase preparation according to Examples 1 and 2, and the XU method described in Example 3.

The characterization was performed in the temperature range of from 40° to 100° C. All assays were performed for 20 minutes at pH 6. The profile is presented in FIG. 3.

Figure 3:
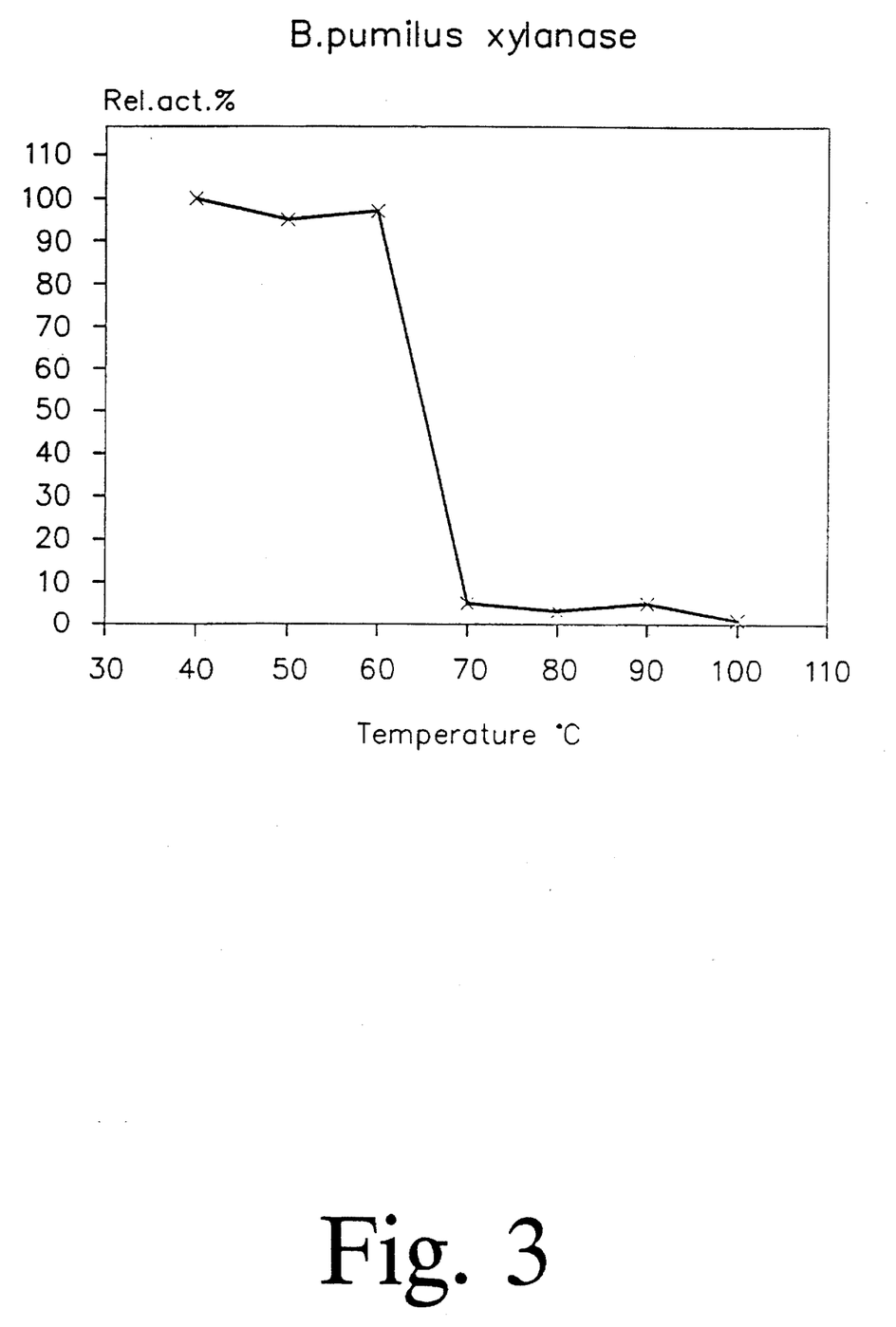
FIG. 3 shows the temperature profile of a xylanase of the invention.
Figure 4:
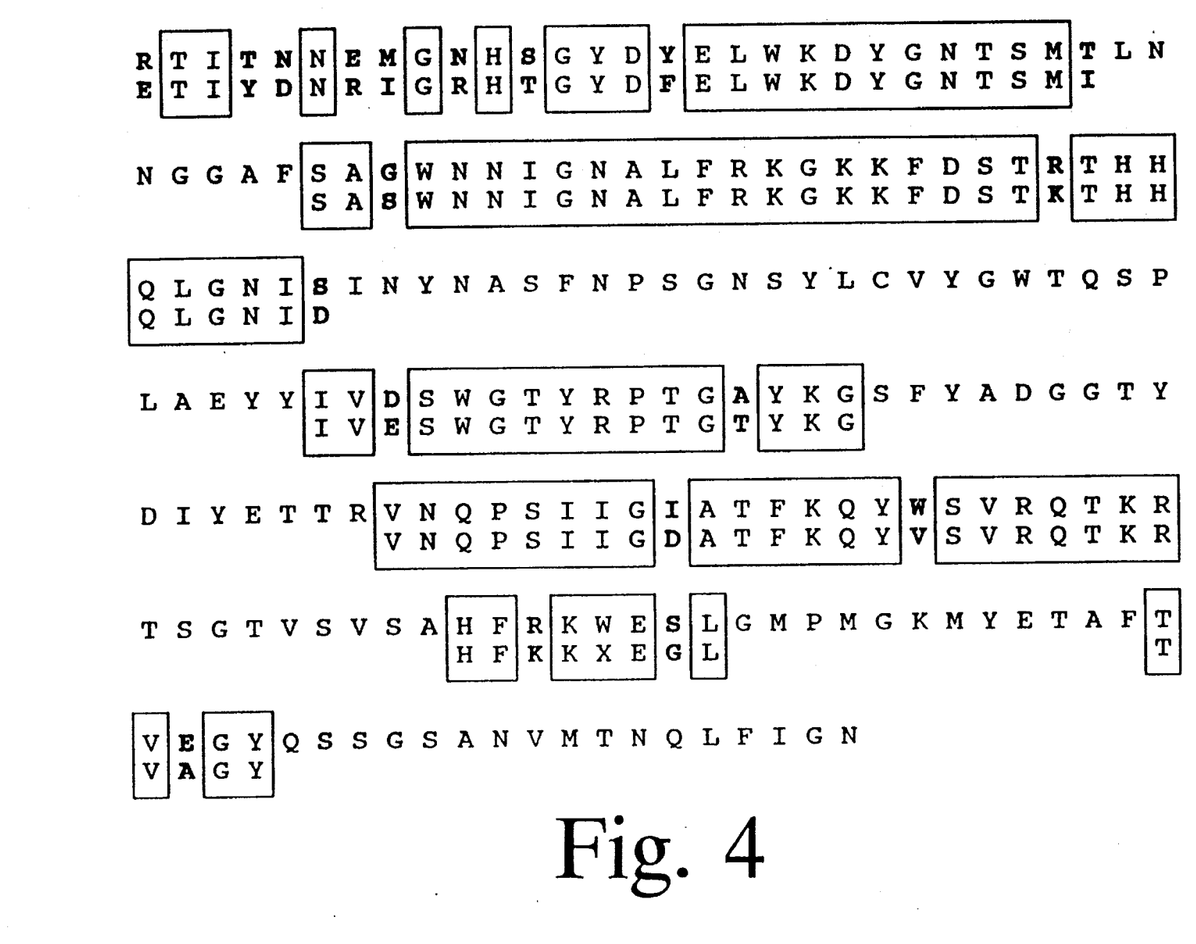
FIG. 4 shows a comparison of the amino acid sequence of the B. pumilus IPO xylanase according to Fukusaki et al. (1984), op. cit. (the upper sequence (SEQ. I.D. No. 1) and the partial amino acid sequence of the xylanase of the invention (the lower sequence (SEQ. I.D. Nos. 2, 3 and 5–8) the amino acids are indicated in the established one-letter code.

It appears from this characterization that the curve for temperature profile is very broad, and that the xylanase has no distinct temperature optimum.

The xylanase is found to be nearly as active at 60° C., with around 95% persisting relative activity, as at 40° C. The temperature optimum is found to be lower than 70° C., where only around 5% of the xylanase activity persist. The optimum is within the range of from 35° to 65° C., more specifically from 40° to 60° C.

EXAMPLE 6 pI characterization

The pI characterization of the xylanase was determined using the purified xylanase preparation according to Examples 1 and 2, and LKB Ampholine PAG plates at pH 3.5 to 9.5.

After electrophoresis, gel was washed twice for 15 min., once in water, once in a Tris-buffer, pH 9, and then overlayered with a thin coat of detection agar consisting of 0.5% of oat spelt xylan, 1% of agarose, pH 9. The overlayered gel was incubated overnight at 50° C.

The xylanase activity was visualised using Congo Red staining (staining for 10 min. with 0.1% Congo Red, and destained for 2 times 15 min. in 1 M NaCl).

The pI for the purified xylanase was found to be above 8, within a range of from 8.0 to 9.5, around 8.8.

EXAMPLE 7

Amino acid sequence

Using standard methods for obtaining and sequencing peptides [Findlay & Geisow (Eds.) (1989); Protein sequencing— a practical approach; IRL Press] derived from the *B. pumilus* xylanase a total of 163 amino acid residues has been identified. In addition, the C-terminal amino acid has been identified as isoleucine.

During direct sequencing of the purified enzyme the N-terminus was found to be partially blocked.

An alignment of the partial sequence of the *B. pumilus* xylanase to the amino acid sequence of the *B. pumilus* IPO xylanase [Fukusaki et al. (1984); op. cit.] is shown in FIG. 1. A total of 26 differences is found and shown in bold typing. Positions in the two sequences which are occupied by identical amino acid residues are outlined. In addition to the 26 differences mentioned above there are two amino acid residues less at the C-terminus of the *B. pumilus* xylanase of the invention than described for the *B. pumilus* IPO xylanase.

EXAMPLE 8

Amino acid composition

The amino acid composition of *B. pumilus* xylanase was determined after acid hydrolysis [Moore & stein (1963); Methods Enzymol. 6, 819–831] using an Applied Biosystems 420A amino acid analysis system. The amino acids in the hydrolysis mixture were quantified using reversed phase HPLC after precolumn derivatization with phenylisothiocyanate [Heinrikson & Meredith (1984); Anal. Biochem. 13.6, 65–74].

The amount of tryptophan was determined spectrophotometrically using the method of Edelhoch [Edelhoch (1967); Biochemistry 6, 1948–1954].

The presence of a single cysteine (Cys) residue in the xylanase was determined through titration with 5,5'-dithiobis-(2-nitrobenzoic acid) [Riddles et al. (1983); Methods Enzymol. 91, 49–60]. The presence of only small amounts of cysteine after acid hydrolysis precludes the presence of disulfide-bridges.

The combined result is shown in Table 1. In addition, a comparison of the amino acid composition of the *B. pumilus* xylanasa with the amine acid composition of the *B. pumilus* IPO xylanase is shown revealing some differences, especially in the content of serine (Ser) and glycine (Gly).

EXAMPLE 9

Treatment of lignocellulosic pulp

An unbleached hardwood brown stock is treated with a hemicellulase preparation from *Bacillus pumilus* (produced according to Example 1) at the following conditions:

| | |
|---|---|
| Time: | t = 3 hours |
| Temperature: | T = 50° C. |
| pH: | pH = 8.0 |
| Consistency: | DS = 10% |
| Dosage: | 715 EXU/kg dry pulp |

After the enzyme treatment the pulp is washed with water and bleached in a three stage bleaching sequence, (D50 C50)E D.

A control is treated in the same way but without addition of enzyme.

Table 2 below shows the kappa numbers of the pulps after the enzyme treatment.

TABLE 2

| | kappa number | reduction % |
|---|---|---|
| Control | 15.0 | — |
| *Bacillus pumilus* | 13.6 | 9.2 |

The (D50 C50)E D bleaching stages are performed under the following conditions:

| (DC)-stage | Time: | t = 20 min |
|---|---|---|
| | Temperature: | T = 50° C. |
| | Consistency: | DS = 5% |
| | Substitution: | 504 with ClO$_2$ (as active chlorine) |
| | Chlorine multiple: | 0.20 |
| E-stage | Time: | t = 1 hr |
| | Temperature: | T = 60° C. |
| | Consistency: | DS = 10% |
| | NaOH dosage: | 2.0% (w/w) on dry pulp |
| D-stage | Time: | t = 3 hr |
| | Temperature: | T = 70° C. |
| | Consistency: | DS = 10% |

Both pulps are bleached to a kappa number of 3,5 after the (D50 C50)E stages, For the control 2,8% (w/w) active chlorine are needed in the (D50 C50)-stage to reach this kappa number, For the enzyme treated pulp only 2,38% (w/w) active chlorine are needed to reach a kappa number of 3,5. This corresponds to a reduction in active chlorine (aCl) of 14,5% for the enzyme treated pulp compared to the control in order to reach the desired kappa number.

In the final D-stage both pulps having a kappa number of 3,5 after (D50 C50)E are bleached to their respective brightness ceilings.

For the enzyme treated pulp a chlorine dioxide dosage of 0.99% (w/w) is needed to bring the pulp to a brightness of 87.2% (ISO) brightness. For the control a dosage of 1.2% (w/w) chlorine dioxide is needed to reach a final brightness of 85% (ISO), This shows that the enzyme treatment makes it possible to reduce the dosage of chlorine dioxide in the final D-stage by 17.5% and at the same time elevates the brightness ceiling of the pulp by a 2.2% ISO brightness.

The enzyme treatment of the pulp neither causes strength nor yield loss.

EXAMPLE 10

Treatment of lignocellulosic pulp

An $O_2$ delignified kraft pine pulp is treated with the purified hemicellulase preparation from *Bacillus pumilus* (produced according to Example 1, and purified according to Example 2) at the following conditions:

| | |
|---|---|
| Time: | t = 3 hours |
| Temperature: | T = 50° C. |
| pH: | pH = 8.5 |
| Consistency: | DS = 10% w/w |
| Dosage: | 815 EXU/kg dry pulp |

The pH was controlled using a Britton-Robinson buffer. After the enzyme treatment the pulp is washed with water and bleached in a two stage bleaching sequence, (D50 C50)E.

A control is treated in the same way but with addition of demineralized water instead of enzyme solution.

Table 3 below shows the kappa numbers of the pulps after the enzyme treatment.

TABLE 3

| | kappa number | reduction % |
|---|---|---|
| Control | 14.9 | — |
| *Bacillus pumilus* | 14.1 | 5.4 |

The (D50 C50)E bleaching stages are performed using 50% substitution with chlorine dioxide at the following conditions:

| | (D50 C50)-Stage | E-Stage |
|---|---|---|
| Temperature: | 40° C. | 60° C. |
| Time: | 15 min. | 60 min. |
| Consistency: | 5% | 12% |

The chlorine multiple in the (D50 C50)-Stage was 0.20, similar to 2.98 % active chlorine (aCl). The amount of NaOH applied in the E-stage is adjusted according to the dosage of active chlorine (aCl) in the (D50 C50)-Stage, i.e. $0.5(\%Cl+\%ClO_2)+0.3=1.8\%$ After the (D50 C50)E stages, the kappa number of the pulp is determined. The results are presented in Table 4 below.

TABLE 4

| | kappa number | reduction % |
|---|---|---|
| Control | 3.50 | — |
| *Bacillus pumilus* | 2.35 | 33 |

The enzyme treatment of the pulp neither causes strength nor yield loss.

This Example demonstrate the bleach boosting effect of a purified enzyme preparation of this invention.

---

We claim:

1. An isolated and purified xylanase which
   (a) is obtained from *Bacillus pumilus* DSM 6124 or a mutant thereof which produces the xylanase;
   (b) has xylanolytic activity in the entire range of 40°–60° C. at pH 6 for at least 20 minutes and has a residual xylanolytic activity of about 95% at 60° C. after 20 minutes; and
   (c) has a pH optimum of 6.

2. The xylanase according to claim 1, which has a molecular weight of 22 kDa as determined by SDS-PAGE.

3. The xylanase according to claim 1, which has an isoelectric point of 8.8.

4. The xylanase according to claim 1 which is obtained from *Bacillus pumilus* DSM 6124.

* * * * *